United States Patent
Teo et al.

(10) Patent No.: US 11,478,798 B2
(45) Date of Patent: Oct. 25, 2022

(54) MICROFLUIDIC DEVICE FOR GENERATING AN IN VITRO LYMPH NODE

(71) Applicant: Khalifa University of Science and Technology, Abu Dhabi (AE)

(72) Inventors: Jeremy C M Teo, Abu Dhabi (AE); Cesare Stefanini, Abu Dhabi (AE); Amal Abdullah, Abu Dhabi (AE); Bisan Samara, Abu Dhabi (AE); Aya Shanti, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 427 days.

(21) Appl. No.: 16/650,218

(22) PCT Filed: Oct. 2, 2018

(86) PCT No.: PCT/IB2018/057638
§ 371 (c)(1),
(2) Date: Mar. 24, 2020

(87) PCT Pub. No.: WO2019/069224
PCT Pub. Date: Apr. 11, 2019

(65) Prior Publication Data
US 2020/0276586 A1 Sep. 3, 2020

Related U.S. Application Data

(60) Provisional application No. 62/566,759, filed on Oct. 2, 2017.

(51) Int. Cl.
*B01L 3/00* (2006.01)
*G01N 33/50* (2006.01)

(52) U.S. Cl.
CPC ...... *B01L 3/502761* (2013.01); *G01N 33/505* (2013.01); *G01N 33/5052* (2013.01);
(Continued)

(58) Field of Classification Search
CPC ......... B01L 3/502761; B01L 2200/027; B01L 2200/0647; B01L 2200/10; B01L 2300/12;
(Continued)

(56) References Cited

U.S. PATENT DOCUMENTS 7,855,074 B2   12/2010   Warren et al.
3,003,387 A1    8/2011   Sukumar et al.
(Continued)

FOREIGN PATENT DOCUMENTS

CN   104306083 A   1/2015
CN   106459898 A   2/2017
(Continued)

OTHER PUBLICATIONS

Rosa et al., The intercell dynamics of T cells and dendritic cells in a lymph node-node-on-a-chip flow device, Lab Chip, 2016, 16, pp. 3728-3740. (Year: 2016).*
(Continued)

*Primary Examiner* — Rebecca M Giere
(74) *Attorney, Agent, or Firm* — Billion & Armitage

(57) ABSTRACT

A 3D microfluidic device for use as an in vitro lymph node is described. The microfluidic device has a body with a semi-circular inner wall and a first channel located adjacent along the semi-circular inner wall, the first channel corresponding to a subcapsular sinus region of a lymph node, a second channel located adjacent the first channel, the second channel corresponding to a reticular network, and a bottom cavity and top cavity, centrally located, corresponding to a paracortex and follicle of a lymph node, respectively. The various compartments of the device are separated by circumferentially and horizontally located rows of micropillars. A lab-on-a-chip device incorporating the microfluidic device is also described.

20 Claims, 6 Drawing Sheets

(52) U.S. Cl.
CPC .... *G01N 33/5088* (2013.01); *B01L 2200/027* (2013.01); *B01L 2200/0647* (2013.01); *B01L 2200/10* (2013.01); *B01L 2300/12* (2013.01); *B01L 2300/123* (2013.01)

(58) Field of Classification Search
CPC ............ B01L 2300/123; G01N 33/505; G01N 33/5052; G01N 33/5088; C12M 23/16
See application file for complete search history.

(56) References Cited

U.S. PATENT DOCUMENTS

| 8,288,159 B2 | 10/2012 | Warren et al. |
| 2016/0075984 A1 | 3/2016 | Hung et al. |
| 2017/0022464 A1 | 1/2017 | Novak et al. |

FOREIGN PATENT DOCUMENTS

| JP | 2012036151 A | 2/2012 |
| WO | 2016083784 A1 | 6/2016 |
| WO | 2017039043 A1 | 3/2017 |
| WO | 2018017605 A1 | 1/2018 |

OTHER PUBLICATIONS

Giese, et al., "Immunological substance testing on human lymphatic micro-organoids in vitro", Journal of Biotechnology 148 (2010) 38-45.
Lubitz, et al., "Human Artificial Lymph Node Model (HuALN)", Encyclopedia of Immunotoxicology, pp. 1-6, 2014.
Search Report and Written Opinion for PCT/IB2018/057638 dated Mar. 15, 2019.
Pearson, et al., "Non-invasive single-cell biomechanical analysis using live-imaging datasets", Journal of Cell Science (2016) 129, 3351-3364 doi:10.1242/jcs.191205.
Extended European Search Report Received, for EP 18864125.2, dated Jun. 24, 2021.
Ross et al., "Spatially resolved microfluidic stimulation of lymphoid tissue ex vivo.". The Analyst, vol. 142(4), 649-659. doi:10.1039/c6an02042a, Feb. 14, 2017.

* cited by examiner

MICROFLUIDIC DEVICE FOR GENERATING AN IN VITRO LYMPH NODE

FIELD OF THE INVENTION

The present invention relates to a biomimetic microfluidic device, and more particularly the present invention relates to a microfluidic device which recreates native human lymph node micro-environment in vitro.

BACKGROUND OF THE INVENTION

An antigen is a substance capable of inducing an immune response. The immune system as already known and understood is a network of cells, tissues and organs that work together against foreign invaders such as bacteria and viruses to protect the human body. The immune system is divided into two sub-systems: the innate immune system and the adaptive immune system. The innate immune system constitutes the first line of defense; it is non-specific to the type of antigen and includes 1) physical barriers such as skin 2) chemical defenses such as the acid in the stomach and 3) cellular attacks induced by phagocytic white blood cells such as macrophages, neutrophils and natural killer cells. On the other hand, the adaptive immune system is specific to the type of antigen and includes lymphocytes known as T cells and B cells. Unlike the innate immune system that is activated immediately upon antigen encounter, the adaptive immune system requires some time to react to a pathogen in case it is newly encountered. Although the innate and adaptive immune systems may seem distinct or extremely different, they are closely linked together. Certain types of antigen presenting cells, namely macrophages and dendritic cells (DCs) mediate the interaction between the two sub-systems. The DCs present antigens to T cells, thus, activates them. Active T cells in turn trigger B cells, leading to the production of antigen-specific antibodies that can destroy pathogens. The encounter of DCs with T cells and their subsequent interaction most often takes place in the lymph nodes, which are oval shaped organs, distributed throughout the lymphatic system that act as filters to remove foreign particles and cancer cells from the body.

Lymph nodes are soft, pale tan, oval shaped, lumpy looking organs distributed throughout the body and act as filters for foreign particles. They have complex structures that enable them to gather large numbers of antigen presenting cells (APCs) and lymphocytes and facilitate their interaction. The basic functional and anatomical unit of the lymph node is the lymphoid lobule. Lymph nodes consist of multiple lymphoid lobules surrounded by fluid filled sinuses and enclosed by a capsule. The lymphoid lobule has two main compartments: the follicle and the paracortex. The follicle houses B cells, whereas the paracortex houses T cells and the DCs. The localization and organization of lymphocytes and DCs within the lymph node is mainly controlled by chemokines, adhesion molecules, and extracellular matrix (ECM) proteins. The lymph node environment can be best described as a densely packed cellular environment with little ECM. The ECM of the lymph node is arranged into an open-weblike system of fibers known as the reticular network. The reticular network is much denser in the paracortex than it is in the follicles. It provides structural support and guidance to APC-lymphocyte interactions. The reticular fibers consist mainly of collagen I and collagen III and support the attachment of a layer of stromal cells called fibroblastic reticular cells (FRCs) via β1 integrin. FRCs ensheath the reticular fibers and join one another with tight junctional complexes to form a "living substrate" onto which T cells and DCs adhere. The FRCs cover around 90% of the reticular fibers, and their organization generates a conduit system that acts as a filter across which small soluble antigens (<70 kDa) can travel. FRCs are not merely structural supports, as they have vital roles in facilitating the migration of lymphocytes and regulating T cell activation. Since within the lymph node, cells crawl but cannot swim and therefore need a road to travel, ECM proteins known to be ligands of lymphocyte adhesion receptors are expressed on the outer surface of FRCs. Moreover, the spacing and orientation of reticular fibers greatly influences the migration rate of lymphocytes.

Naive B and T cells extravasate into the lymph nodes via high endothelial venules (HEVs) or afferent lymphatic vessels. In general, once in the Lymph node, T cells randomly crawl along FRCs in the paracortex, whereas B cells crawl on FRCs to reach the follicles. Inside the follicle, B cells pack within follicular DCs (FDCs) forming a dense network in which B cells search for antigens. B cells do not get stimulated instantly when encountering antigens. Instead, they accumulate antigens over time, suggesting "multiple rounds of antigen acquisition". It is the DCs which are APCs that recognize and process antigens from tissues, and present them to T cells in the lymph nodes. The DCs that are associated with the lymph node can be divided into two main categories: resident DCs and migratory DCs. Resident cells reside in the T cell zone (paracortex) of the lymph node in close proximity to FRC conduits. They rapidly take up soluble antigens from the lymph fluid and present it to lymphocytes. On the other hand, migratory DCs travel from tissues to lymph nodes via afferent lymphatic vessels carrying high concentrations of processed antigens. They then localize near HEVs to increase the probability of encountering naïve lymphocytes.

Lymphatic fluid, is a fluid similar to blood plasma that contains lymphocytes, migratory DCs, waste products, cellular debris, bacteria and proteins that enters the lymph nodes through the afferent lymphatic vessels in order to get filtered. From the afferent vessel, the lymphatic fluid subsequently travels through a number of smaller sinuses: the subcapsular sinus (SCS), the trabecular sinus, the medullary sinus through which it gets cleaned and finally leaves the lymph node at the hilus through the efferent lymphatic vessel. FRCs are situated close to the SCS where they can capture and transport antigens from the lymph fluid to the nearby-lying APCs. Particularly, the lymph nodes usually have one efferent vessel and multiple afferent ones. This allows the lymph node to act as a "settling tank" providing sufficient time for lymphocytes to recognize antigens and interact with APCs.

In the biomedical and pharmaceutical fields, new drugs are continuously researched and developed in an attempt to combat pathogens and disease causing agents. However, Pharmaceutical drug development industry faces high attrition rates for novel drug candidates. The concluding statement from an intra-establishment study, involving major pharmaceutical companies AstraZeneca, Eli Lilly, GlaxoSmithKline and Pfizer, is that while improved analytical methods and experimental methodologies have enhanced drug metabolism and pharmacokinetic profiles, failures due to efficacy and safety have maintained attrition rates. Drugs that have passed and deemed commercially profitable have been tagged with an estimated USD 1.7 billion developmental cost. One key aspect along the development chain that has been overlooked is the effect of the drug candidate on our immune system. In-depth investigations into this aspect are lacking and it could unlock significant knowledge to economize the high cost as well as reduce the attrition rate, largely through the mechanistic understanding of our immune physiology to drugs.

All types and all classes of pharmaceutical drugs perturb the immune system (Kidd et al., 2015), but the mechanisms and immunological outcomes of these perturbations are not well defined. Lack of understanding on these biological-pharmaceutical interactions confounds drug development, conceals potential side effects and limits discovery. In addition, the latest pillar in the drug industry that is currently medicine's latest revolution is the use of immune cells for cell-based drug delivery, which is superior compared to many other delivery systems and have broad applicability. Similarly, further evaluation needs to be performed on such modified immune cells, as the introduction of cell carriers to deliver drugs could interrupt natural physiological conditions or exacerbate already diseased tissues.

Mechanistic studies of cellular systems are best-performed using experimental setups that facilitate the addition and/or removal of components from the cellular microenvironment. Such controlled setups are possible with microfluidic technology, which has been widely employed to biology research to reduce cost of reagents and maximize information from precious samples, simultaneously provide spatio-temporal dynamics of the cell in their microenvironment.

Various microfluidic models have been developed in the past to recreate the tumor microenvironment and that of the blood-brain barrier and others. Literature indicates that the attempts to build an in vitro lymph node are limited and each has its own approach. In their patented "Artificial Immune System" (U.S. Pat. No. 8,288,159 B2). William Warren et. al introduce a whole artificial immune system that consists of three tissue equivalents: a) skin equivalent b) a lymphoid tissue equivalent and c) blood vascular network equivalent, all of which are enclosed in a bioreactor with a controlled environment. The movement of cells, mainly dednritic cells, from one tissue equivalent to the other is controlled via magnetic microbeads and nanobeads. However, the addition of micro/nano beads could artificially invoke an unnecessary immune response and probably minimize the effectiveness of the system in mechanistic studies. For the lymphoid tissue equivalent, the following designs are presented: (1) a mockup image of a digitally printed lymph node using BioAssembly Tool in which the distinct T and B cell areas are maintained via microsphere releasing T and B cell attractants and (2) T and B cell-populated microcarriers enclosed in a porous container. Although the approach of the first design, i.e. bioprinting is quite promising, the use of microspheres to guide the organization of the T and B-cells may induce an unnecessary immune response, and thus affect the fidelity of the system. The second design, on the other hand, does not closely mimic the anatomy of the in vivo lymph node and seems to limit the interaction between the different cell types as they are situated on microcarriers.

An extension of the previous patent (U.S. Pat. No. 8,003, 387 B2) was introduced in 2011. The inventors aimed to examine the humoral immune responses to vaccines, allergens, and other agents, through in vitro germinal centers (GCs), which are mature follicles. Their system consists of at least one 3D germinal center (comprising follicular DCs, B cells, and T cells) embedded in or fixed on an engineered tissue construct, which could be made of collagen, gelatin, hyaluronic acid, or other ECM material. Their approach includes placing antigen-loaded follicular DCs in the engineered tissue construct containing naïve lymphocytes, to induce an immune response. However, this has system had many drawbacks. Firstly, important components of the lymph node such as the sub capsular sinus, reticular network, and paracortex, follicle of the lymph node were missing. As a result, U.S. Pat. No. 8,003,387 B2 was limited to the study of humoral immune responses, but not the cell-mediated immune responses. Secondly, cell-loaded antigens are manually placed into the lymphoid organ equivalent, which is the GC in this case, while in vivo, antigens enter the lymph node via the lymphatic fluid, and throughout their journey in that lymph node they might be caught by lymphocytes and subsequently initiate an immune response. Thirdly, the invention disclosed in U.S. Pat. No. 8,003,387 B2 is limited to static conditions and does not support flow.

Another recent patent WO2016083784 A1 titled "Lymph Node replacement construct" discusses a lymph node replacement model that consists of three parts: one or more inlets, a body, and one or more outlets. The body in turn comprises an internal structure defining one or more fluid communication paths extending from the inlet or inlets, to the outlet or outlets. The model further incorporates small valves to ensure a unidirectional flow of fluid. However, this model has been proposed as a replacement of the actual in vivo lymph node for patients whose lymph node has been surgically removed and that eventually develop edema due to a reduction in fluid drainage. The model therefore, serves the function of maintaining the physiological flow rate of the lymphatic fluid and does not incorporate any cellular components.

On the other hand, Annika Lubitz and Christoph Giese present a bioreactor-based model of the lymph node. Their approach involves co-culturing lymphocytes, DCs and stromal cells on a 3D based matrix within the bioreactor that is perfused, oxygenated and fed. The bioreactor hosts two continuously perfused cell culture compartments separated by a double membrane. Despite its potential, the model does not closely mimic the anatomy of native lymph node and thus, undermines immune competence of cells.

None of the existing patents or available designs offer a comprehensive model of the in vivo lymph node that is capable of replacing animal testing, and is easily reproducible and user friendly at the same time. Since, the lymph node is the meeting center for immune cells, whereby the body invokes immune responses to guard against foreign substances, there is a need to develop an in vitro model of the lymph node that closely mimics its microenvironment in order to facilitate mechanistic studies of cell-cell interactions and immunological responses and thus provide better predictability of the efficacy, efficiency and toxicity of newly developed drugs. Further, there is also a need to develop an in vitro lymph node that incorporates the important cellular components of human lymph node and provides for cell mediated immune responses.

SUMMARY OF THE INVENTION

Therefore, it is an object of the present invention to provide for an in vitro lymph node that facilitates investigations into immune cell-cell interactions and downstream immunological responses, thereby providing information on the immunotoxicity of newly developed drugs.

It is also an object of the present invention to provide a device which mimics the anatomy and physiology of the human lymph node environment as closely as possible.

It is a further object of this invention to provide a device mimicing the lymph node anatomy while successfully sustaining cell viability.

It is an additional object of the present invention to provide a device which supports live-imaging, and allows real time monitoring of the lymph node activity within the device.

It is also an object of the present invention to provide a user friendly and easily manufactured device which can be implemented in various biomedical and pharmaceutical applications for studying the activities of various antigens and physical responses occurring within a lymph node environment.

In one aspect of the present invention, a microfluidic device is disclosed for generating an in vitro lymph node, the device comprising a first channel, a second channel located adjacent to the first channel, a bottom cavity and a top cavity centrally located within the device, wherein the microfluidic device mimics the anatomy and physiology of the lymph node.

In an embodiment, the first channel corresponds to a subcapsular sinus region of a lymph node, the second channel corresponds to a reticular network of a lymph node, the centrally located bottom cavity corresponds to a paracortex of a lymph node, and the centrally located top cavity corresponds to a follicle of a lymph node In an embodiment, the microfluidic device further comprises an inlet aperture and an outlet aperture.

In an embodiment, the inlet and the outlet aperture allow for injection of at least one of fluid, gas and solid materials within and through the microfluidic device.

In an embodiment, the microfluidic device is directly filled with cellular components in the first channel, the second channel, the top and the bottom cavity.

In an embodiment, the microfluidic device further comprises, an outer surface for sealing the device to a support base. In a preferred embodiment, the support base is a glass support base.

In a further embodiment, the sealed microfluidic device has open inlet and outlet holes, allowing for injection of at least one of fluid, solid and gas material within the microfluidic device.

In an embodiment, the body of the microfluidic device is fabricated with a material selected from a group consisting of glass, silicon, polysiloxane, optically transparent polymers.

In a preferred embodiment, the polysiloxane used to fabricate the microfluidic device is polydimethylsiloxane (PDMS).

In another embodiment, the width of the first channel of the microfluidic device is smaller than the width of the second channel.

In an embodiment, the first channel and second channel of the microfluidic device are separated by circularly distributed micro-pillars.

In another embodiment, the bottom cavity and top cavity of the microfluidic device are separated by a horizontal row of micro-pillars.

In an embodiment, the diameter of a diameter of the micro-pillars is at least 0.45 mm. In another embodiment, the height of the micro-pillars is at least 1.5 mm.

In an embodiment, hydrogels are contained separately within the first channel, second channel, bottom cavity and top cavity of the microfluidic device.

In a preferred embodiment, the hydrogel is Type I collagen hydrogel.

In a preferred embodiment, the microfluidic device comprises B cells in the top cavity and T cells in the bottom cavity.

In another aspect the present invention also discloses, a lab-on-a-chip comprising the microfluidic device, comprising a first channel, a second channel located adjacent the first channel, a bottom cavity centrally located within the device, a top cavity centrally located within the device, wherein the microfluidic device mimics the anatomy and physiology of the lymph node.

In an embodiment, the lab-on-a-chip comprising the microfluidic device comprises the first channel which corresponds to a subcapsular sinus region of a lymph node, the second channel which corresponds to a reticular network of a lymph node, the centrally located bottom cavity which corresponds to a paracortex of a lymph node, and the centrally located top cavity which corresponds to a follicle of a lymph node.

In an embodiment, the lab-on-a-chip comprising the microfluidic device comprises an inlet aperture and an outlet aperture that allows for injection of at least one of fluid, gas and solid material within and through the device.

In an embodiment, the lab-on-a-chip comprising the microfluidic device is directly filled with cellular components in in the first channel, the second channel, the top and the bottom cavity, and then sealed with a transparent support base.

In another embodiment, the width of the first channel of the microfluidic device is smaller than the width of the second channel.

In an embodiment, the lab-on-a-chip comprising the microfluidic device is fabricated with a material selected from a group consisting of glass, silicon, polysiloxane, optically transparent polymers.

In a preferred embodiment, the polysiloxane is polydimethylsiloxane (PDMS).

In another embodiment, the first channel and second channel of the microfluidic device forming the lab-on-a-chip are separated by circularly distributed micro-pillars.

In an embodiment, the bottom cavity and top cavity of the microfluidic device forming the lab-on-a-chip are separated by a horizontal row of micro-pillars. The diameter of a diameter of the micro-pillars is at least 0.45 mm. In another embodiment, the height of the micro-pillars is at least 1.5 mm.

In an embodiment, the top cavity of the microfluidic device forming the lab-on-a-chip comprises of B cells and the bottom cavity of the microfluidic device forming a lab-on-a-chip comprises of T cells.

In an embodiment, the collagen hydrogels are contained separately within the first channel, second channel, bottom cavity and top cavity of the microfluidic device forming the lab-on-a-chip.

BRIEF DESCRIPTION OF THE DRAWINGS

The subject matter that is regarded as the invention is particularly pointed out and distinctly claimed in the claims at the conclusion of the specification. The following drawings form part of the present specification and are included to further demonstrate certain aspects of the present invention, the inventions of which can be better understood by reference to one or more of these drawings in combination with the detailed description of specific embodiments presented herein. The foregoing and other aspects, features, and advantages of the invention are apparent from the following detailed description taken in conjunction with the accompanying drawings in which:

DETAILED DESCRIPTION OF THE INVENTION

Figure 1:
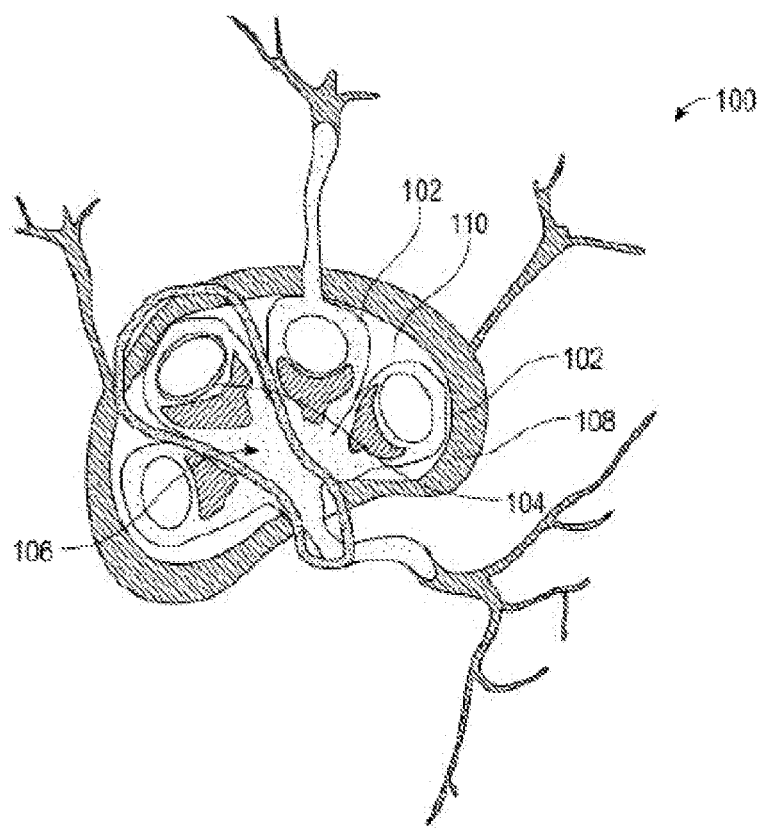
FIG. 1 illustrates a lymph node showing multiple lymphoid lobules—each lymphoid lobule consists of a follicle and a paracortex.

In the following Detailed Description, reference is made to the accompanying drawings, which form a part hereof, and in which is shown by way of illustration specific embodiments in which the invention may be practiced. Wherever possible, the same reference numbers are used in the drawings and the description to refer to the same or like parts. Directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Some preferred embodiments of the invention described herein relate generally to prosthetic and orthotic systems. While the description sets forth various embodiment-specific details, it will be appreciated that the description is illustrative only and should not be construed in any way as limiting the invention. Furthermore, various applications of the invention, and modifications thereto, which may occur to those who are skilled in the art, are also encompassed by the general concepts described herein The present invention aims to provide a microfluidic device for an in vitro lymph node wherein the microfluidic devices include the efficient consumption of reagents, high-throughput analysis, miniaturization of components, and relatively low cost of fabrication.

The present invention also aims, to provide for a microfluidic device which mimics the anatomy and physiology of the human lymph node, sustains cell viability, enables live-imaging, and is user-friendly. The microfluidic device of the present invention is multicompartmentalized incorporating selected cell types especially B cells and T cells found in the human lymph node that are crucial to immunity. The microfluidic device as disclosed allows for sufficient amounts of gas exchange within the lymph node model to sustain cell viability. In addition, the microfluidic device as disclosed is durable, robust and very sturdy to handle.

The present invention provides for a PDMS fabricated microfluidic device, which is easy to synthesize with variable stiffness, relatively inexpensive, allows surface treatment to modulate its hydrophobicity.

The microfluidic device as provided in the present invention is sealed with a transparent glass base, to hold the added fluids or hydrogels without compromising the optical clarity of microscopic imaging. In addition, the microfluidic device disclosed is inert, so it does not interfere with cultured cells and provides the ability to create precise and carefully controlled chemo-attractant gradients that allow the study of motility, chemotaxis and the ability to develop resistance to antibiotics in small populations of microorganisms and in a short period.

FIG. 1 illustrates a lymph node (100) showing multiple lymphoid lobules (102)—each lymphoid lobule (102) consists of a follicle (104), a paracortex (106), a subcapsular sinus region (108) and a reticular network (110).

Figure 2A:
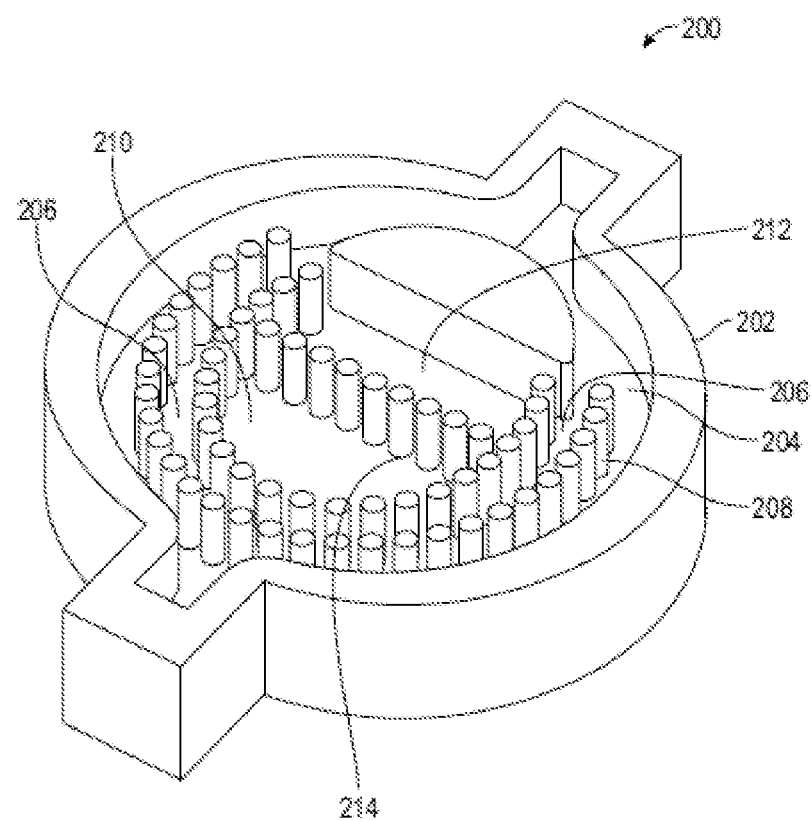
FIG. 2A illustrates 3D AutoCAD model of the theoretical design of the microfluidic device

FIG. 2A illustrates a 3D AutoCAD model of the theoretical design of the microfluidic device (200) as disclosed above showing the different regions if the device (200) such as a first channel (204) located adjacent along the semi-circular inner wall (202), a second channel (206) located adjacent to the first channel (204); wherein the first channel (204) and second channel (206) are separated by circularly distributed micro-pillars (208), a bottom cavity (210) and a top cavity (212) centrally located within the device (200), wherein the bottom cavity (210) and top cavity (212) are separated by a horizontal row of micro-pillars (214). The inner wall (202) of the microfluidic device (200) can be of other shapes such as circular, semi-circular, elliptical.

Figure 2B:
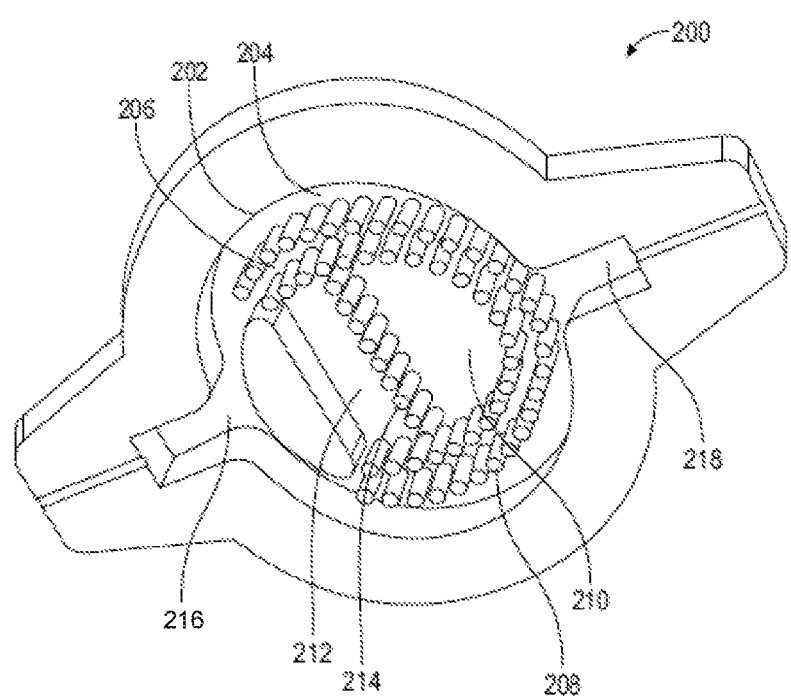
FIG. 2B illustrates a silicone based microfluidic device fabricated from the inversely-machined mold

FIG. 2B illustrates a mold of a microfluidic device (200). The microfluidic device (200) comprises of a body with a semi-circular inner wall (202), a first channel (204) located adjacent along the semi-circular inner wall (202), a second channel (206) located adjacent to the first channel (204); wherein the first channel (204) and second channel (206) are separated by circularly distributed micro-pillars (208), a bottom cavity (210) and a top cavity (212) centrally located within the device (200), wherein the bottom cavity (210) and top cavity (212) are separated by a horizontal row of micro-pillars (214).

Further, microfluidic device (200) comprises the inlet aperture (216) and an outlet aperture (218). The microfluidic device (200) is designed and enabled to mimic an in vitro lymph node as each channel and cavity within the device (200) corresponds to a lymph node (100) component such as the first channel (204) corresponds to a subcapsular sinus region (108) of the lymph node (100) wherein large antigens (>70 KDa) are supposed to flow. The second channel (206) of the device (200) corresponds to a reticular network (110) of a lymph node (100). The second channel (206) filled with a specific porous extra cellular matrix that is able to trap small soluble antigens and that facilitates the migration of migratory DCs from the lymphatic fluid towards lymphocytes. The extra cellular matrix comprises of hydrogels, proteins or combination of proteins such as Collagen I, Collagen III, Collagen IV, elastin, fibronectin, laminin-1, tenascin, vitronectin, and heparin sulfate.

The second channel (206) is separated from the first channel (204) by PDMS micro-pillars (208). It is assumed that the PDMS micro-pillars (208) would allow for the incorporation of different extra cellular matrix components while maintaining their separation.

The centrally located bottom cavity (210) corresponds to a paracortex (106) of a lymph node (100) and the centrally located top cavity (212) corresponds to a follicle (104) of a lymph node (100). In addition, the bottom cavity (210) and a top cavity (212) are separated by PDMS micro-pillars (214). The top cavity (212) is where B-cells reside and a bottom cavity (210) where T-cells and resident DCs reside. Each of these two cavities (210, 212) will be filled by a particular extra cellular matrix and will contain the specific chemokines required for B-cell and T-cell organization/assembly (chemoattractant associated with B-cell assembly: CXCL13 and chemo-attractants associated with T-cell assembly: CXCL12, CCL21 and CCL19).

In one embodiment of the present invention, the microfluidic device (200) contains an inlet aperture (216) which corresponds to the afferent vessels of the lymph node (100) and an outlet aperture (218) which corresponds to the efferent vessel of the lymph node (100). These inlet aperture (216) and outlet aperture (218) allow for flow of fluids through the microfluidic device (200).

Further, the microfluidic device (200) also comprises an outer surface (220) which is adapted to be sealed to a glass support base tightened using sterile mechanical screws to create a perfect seal.

In one embodiment, the body (202) of the microfluidic device (200) is fabricated of a material selected from silicon or other optically transparent polymer materials.

The first channel (204), second channel (206), and the centrally located bottom cavities (210) and top cavities (212) are adapted to separately contain and/or channel various fluid, solid or gas materials of varying composition and concentration, through the separation provided by the circularly distributed micro-pillars (208) and horizontal row of micro-pillars (214) within the device (200). The physical separation between different regions is achieved by PDMS micro-pillars (208, 214), to allow for the incorporation and interaction of different components while maintaining their separation.

With respect to dimensions, the diameter of the micro-pillars (208, 214) is preferably around 0.45 mm and the height of the micro-pillars is about 1.5 mm. The micro-pillars (208, 214) can have a height of about 1.5 mm and the separation from micro-pillar to micro-pillar is about 0.2 mm. The diameter of the body (202) as defined by the semicircular inner wall is about 1.1 cm.

In preferred embodiment, the device (200) is comprised of optically transparent material for enabling imagining and optical monitoring of the device (200) and contents therein within the first channel (204), second channel (206), the bottom cavity (210) and the top cavity (212), so that live- or recorded imaging of the activity can be achieved in order to monitor and study the activity of particular biological interactions within the in vitro lymph node environment, such as for example the study of APC-lymphocyte interaction. Hydrogels can be placed within the various compartments of the microfluidic device (200), including the first channel (204), the second channel (206) and the centrally located bottom cavity (210) and top cavity (212). This can be achieved through directly placing the hydrogels in the desired compartments prior sealing the device.

In another aspect, the present invention also discloses a lab-on-a-chip device comprising the microfluidic device (200) as described above.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims, which follow.

EXAMPLES

Preparation of the Mold for the Microfluidic Device

Sizes of in vivo lymph nodes vary between 0.5 cm to 2.0 cm depending on the location and activation level of the node. Under abnormal conditions, such as inflammation or cancer, some LNs may expand as the immune system reacts to the problem. In the present invention, the inventors assumed a fixed size of the lymph node, which is around 1.1 cm excluding the walls of the device. However, the user can still change flow rates to resemble the desired condition, which is equivalent to the changing lymphatic fluid influx in the in vivo lymph node. The user may increase the flow rate in the device to study cellular responses during inflammation.

Once the specific dimensions of the different parts of the microfluidic device were finalized, an AutoCAD 3D model of the device was generated. The AutoCAD design as exhibited in FIG. 2A forms the basis for generating a mold, which is then used to fabricate the PDMS based microfluidic device. The first step of fabrication is converting the CAD design to a G-code, which is numerical control programming language used mainly in computer-aided manufacturing to control automated machine tools. The G-code in turn guides an automated machine to etch the desired design (with the desired compartments and channels) onto a polytetrafluoroethylene (PTFE) piece generating a PTFE mold, which is then used to fabricate the PDMS based microfluidic device. FIG. 2B illustrates a PDMS based microfluidic device describing the various compartments corresponding to the in vivo lymph node. The fabrication of the PTFE mold was done using CN-MAX 80-45 machine (TEA Technology Engineering Automation SRL, Pisa), and the process involved four main steps: 1) Positioning the mill (cutting apparatus) of the machine on the center of the PTFE piece; 2) Smoothening the surface of the PTFE piece using a special mill (to prevent the formation of voids or other defects in the PDMS after it is poured onto the mold); 3) Puncturing holes that would give rise to the pillars using a 0.45 mm drill; 4) Making the "D"-shaped section and the outer wall of the design using an appropriate mill, subsequent to which the PTFE model is fabricated.

FIG. 2 B illustrates the successfully fabricated mold of the PDMS based microfluidic device representing each component in the in vivo lymph node.

Fabrication of Microfluidic Device

The fabrication of a PDMS microfluidic device as described above is simple and relatively inexpensive. The procedure involves creating a mold with the desired channels or compartments. The mixture of PDMS and a cross-linking agent, to cure the PDMS, is poured into the mold and heated at a specific temperature of approximately 65° C. Once the PDMS hardens, it is taken off the mold. A replica of the micro-channels are obtained on the PDMS block. The PDMS device is then treated with oxygen plasma to convert its surface from hydrophobic to hydrophilic, and support the adhesion of hydrogels. Desired cellular components embedded in hydrogels of choice are filled in the different compartments of the device. Then the device is sealed with a glass base tightened using sterile mechanical screws to create a perfect seal.

The microfluidic device is then ready to be connected to microfluidic reservoirs and pumps using microfluidic tubing.

Various assessments were carried out to prove that the final prototype is a working and practical model of the human lymph node. More specifically, the microfluidic device mimics the in vivo lymph node by providing separation between different compartments, maintains cell viability, and sustains different flow rates.

Assessment of Cell Viability

In order to prove that device of the present invention, or the process of putting cells in it does not cause cell death, we tested cell viability overnight. B and T lymphocytes were injected in the compartments bottom and the top cavities of the device respectively, while compartments while the first and the second channel were filled with media to humidify the environment and enhance gas exchange to sustain cell viability. Then different positions in the device were imaged at 5×.

Quantification of the obtained images was done by manually tracking the two cell types using Fiji developed by the scientific image analysis platform Image J. Several cells were marked, and the coordinates of each cell was taken at each slice of the video. After that, the distance travelled by each cell between consecutive slices was calculated using the formula:

$$\text{Distance} = \sqrt{(x_2-x_1)^2+(y_2-y_1)^2}.$$

Figure 3:
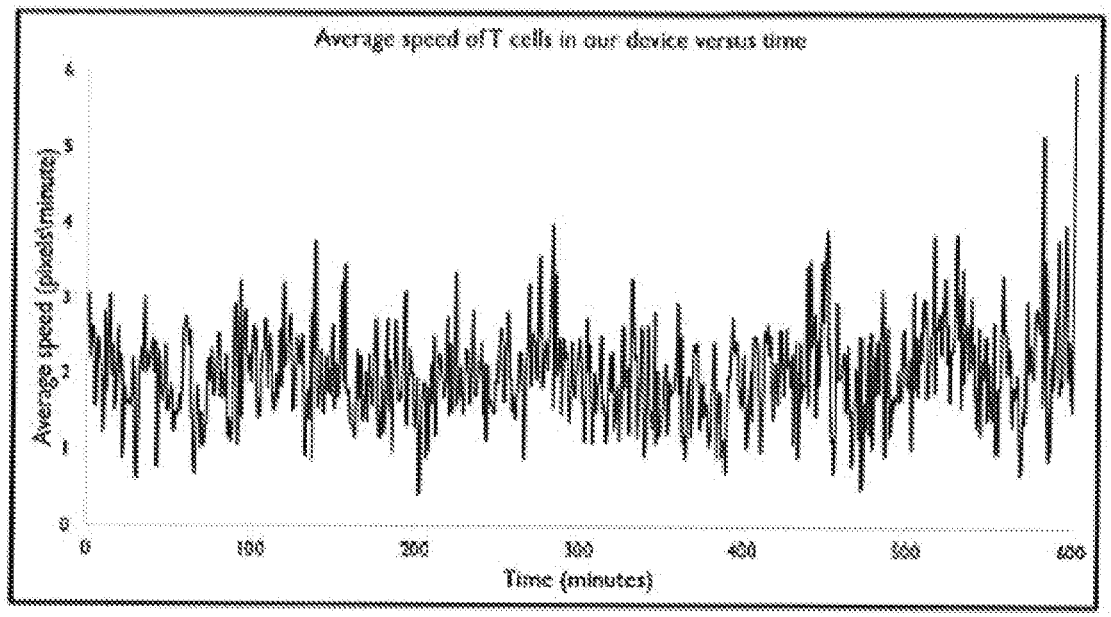
FIG. 3 illustrates a plot of average speed of T cells (in pixels/minute) within the device.
Figure 4:
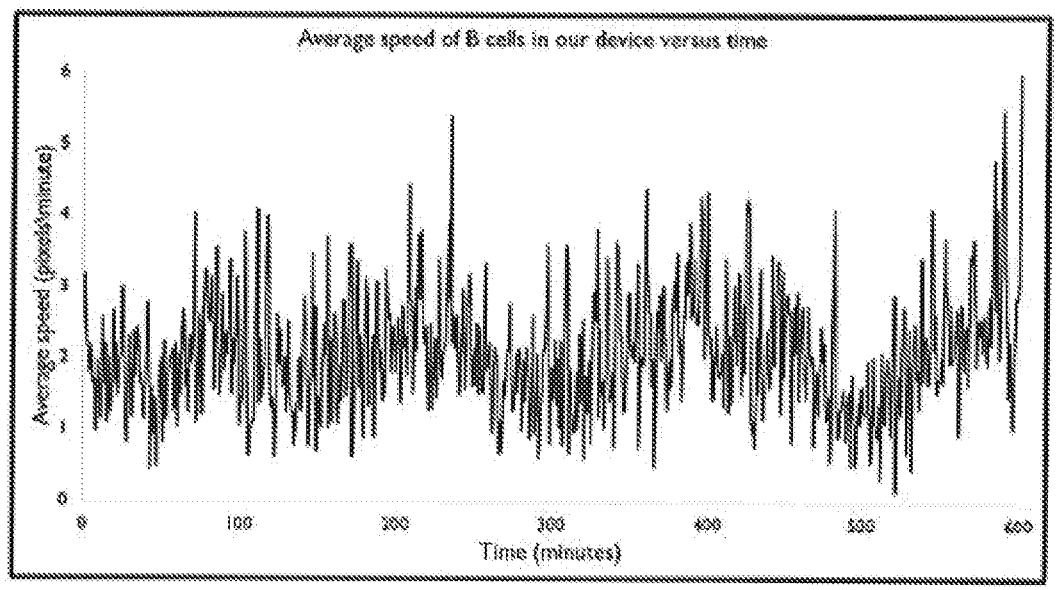
FIG. 4 illustrates a plot of average speed of B cells (in pixels/minute) within the device.

Then the speeds were obtained by dividing the distance over time, the latter was set to be 1 minute between each slice and the other. The average speed of each of T and B cells was then plotted versus time, as seen in FIGS. 3 and 4 respectively. Both cell types kept moving with varying speeds the entire imaging duration, and the speeds did not decline, indicating that the cells are viable and did not undergo apoptosis. Furthermore, cells were placed within the device along with media, incubated for 24 hours and their viability was quantified via flow cytometric analysis. The results indicate that cells remained viable for the whole duration with less than 9% cell death. This proves that the material of the device itself and the entire process of hydrogel filling, flow injection, and imaging is safe for cells.

In the plot depicted in FIG. 3, which shows the average speed of T cells in pixels/minute, it can be seen that the speed did not decline to zero, indicating that the cells are viable, and in continuous movement. In FIG. 4, it can be seen through the plot of average speed of B cells in pixels/minute, that the speed did not decline to zero, indicating that the cells are viable, and in continuous movement.

Assessment of Flow Rates

Before assessing flow in our device, the flow was simulated in our device through a Computational Fluid Dynamic (CFD) simulation developed using ANSYS R17.2 (ANSYS, Inc, United States). Two variables were quantitatively studied in our device: speed of the flow and pressure.

Figure 5:
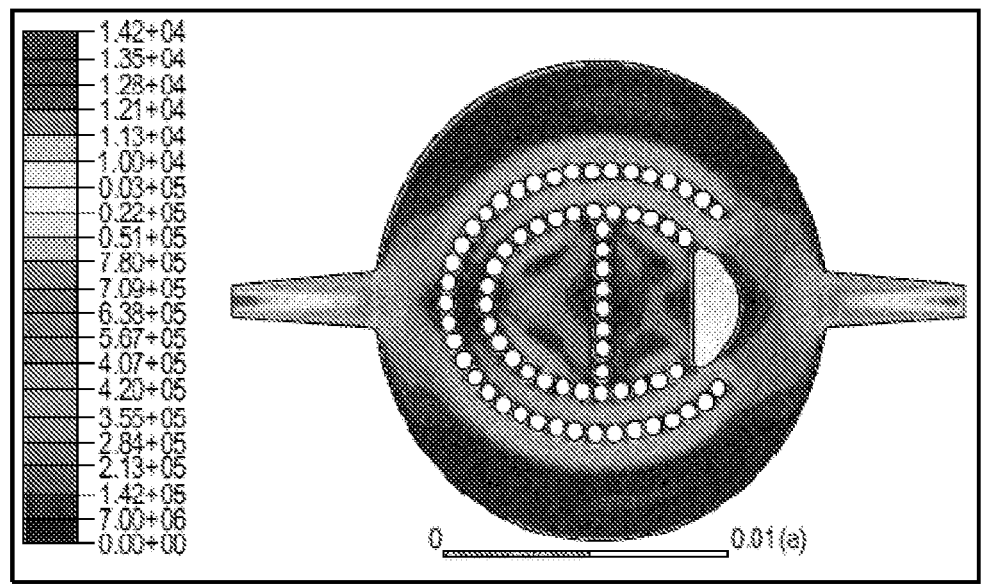
FIG. 5 depicts a CFD simulation of the flow speed in the device produced using ANSYS R17.2.

FIG. 5 shows the CFD result of speed analysis. The highest speeds are at the inlets and outlet, which is expected since they are the paths of the smallest diameter. Once the flow exists the inlet and enters the device, its speed decreases dramatically due to the resistance posed by the gels. Notice that in most parts of the device the speed is low to moderate. In fact, the geometry of the device was designed in a way that decreases the speed of the flow in the top and bottom cavities (the cellular regions), as proved in the figure, to give more time for the cells to interact with the substances being inserted with along with the flow.

Figure 6:
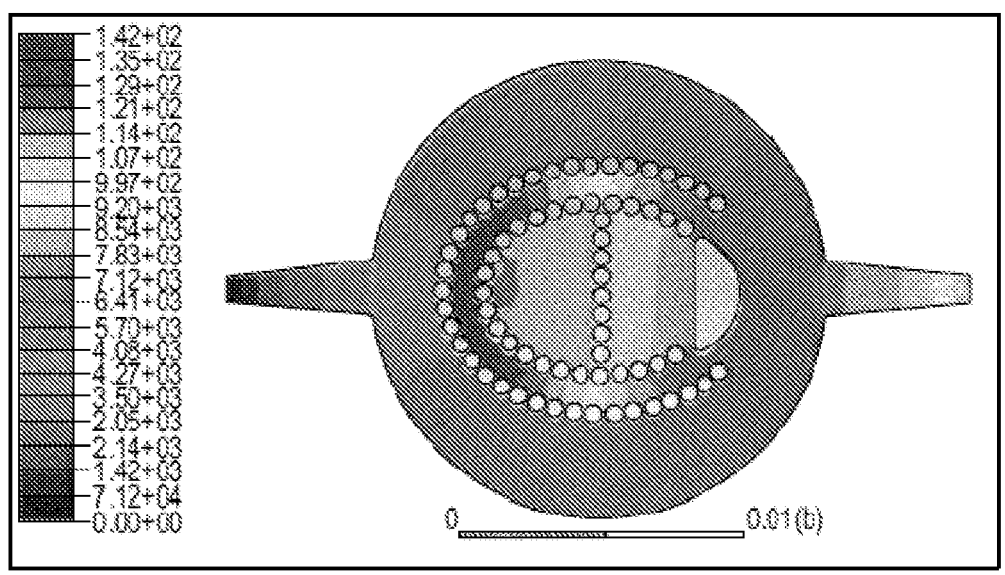
FIG. 6 illustrates a CFD simulation of the pressure in the device produced using ANSYS R17.2.

FIG. 6 shows the CFD result of pressure analysis. The highest pressure is at the end of peak of channel 2, which is expected since this is where the flow converges in order to exit the device. Otherwise, the pressure is relatively moderate in most regions.

Figure 7:
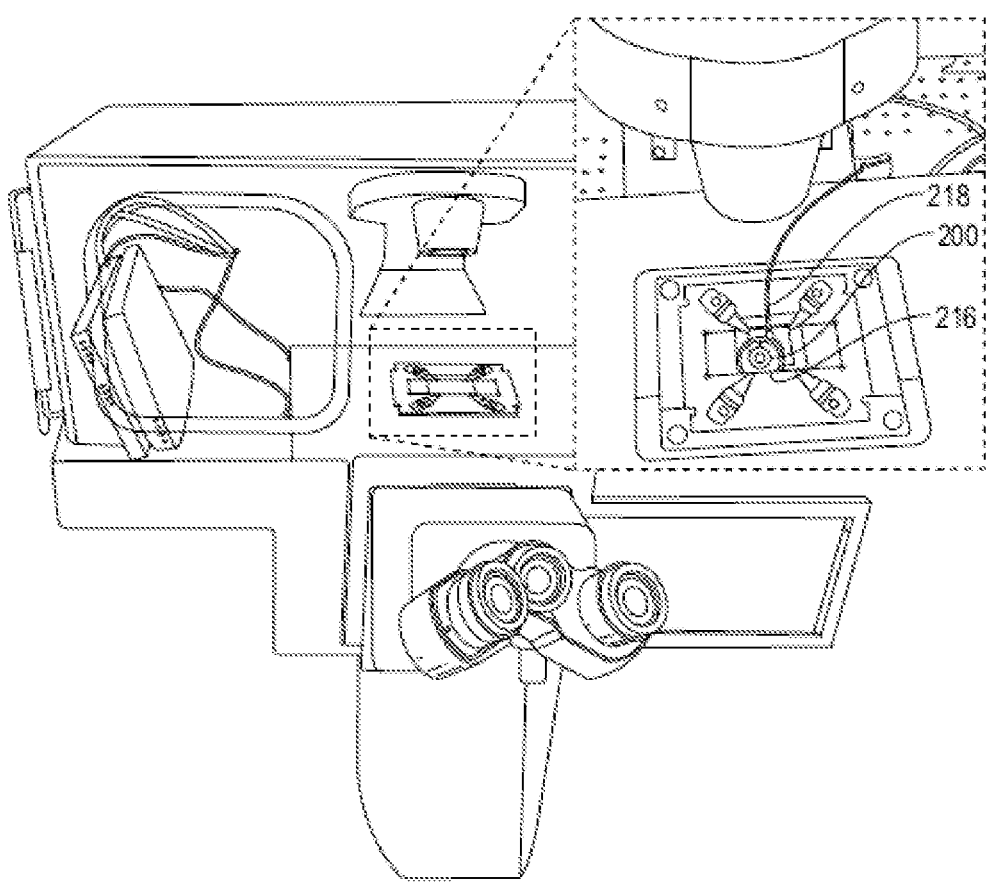
FIG. 7 illustrates setup of the flow rate assessment experiment.

FIG. 7 shows a setup of the flow rate assessment experiment. The device is placed under the microscope. The inlet aperture of the device is connected to a syringe via tubes. The syringe is placed in a pump to control the flow rate. The outlet aperture of the device drains the fluids outside the device.

By assessing the flow proved the following:

Injected fluid moves through the gels of different concentration: It is important to make sure that the fluid does not take the path of least resistance, which is the interface between the gels and the glass. This was achieved by allowing the gels to polymerize inside the device, thus, forming a chemical bond with the glass. Consequently, the fluid is forced to move through the gels. This result was proven experimentally by the observation that some nanoparticles were trapped in the gel, in addition to observing the particles moving in 3D across the gels.

The flow covers all regions of the device: Nanoparticles were observed flowing all over the device. This is crucial for any application of the device. For example, if the injected fluid is media, then it is important that it reach all the cells in different compartments of the device.

The injected fluid converges and exists at the outlet: The fluid should not be trapped inside the device but to flow smoothly reaching the outlet. Monitoring the flow showed that the nanoparticles exiting the device.

The device sustains various flow rates without displacing the gels, or leaking. Furthermore, this result proves the versatility of the device for different user applications. For instance, the device sustains high flow rates that could resemble lymph node inflammation.

Overall, the constructed microfluidic device eliminates previous drawbacks in the art. The designed embodiments mimic the anatomy and physiology of the human Lymph node since it is a multi-compartmentalized microfluidic device that is able to incorporate crucial immune cells; such as B cells, T cells, and DCs. Moreover, based on tests conducted, the device allows sufficient amount of gas exchange, and could be easily sterilized to sustain cell viability and prevent cell death. Furthermore, it enables live imaging because it fits within a standard glass slide, and its setup does not disperse the microscope light, resulting in high quality images. Finally, the device is durable, robust, sturdy for handling, and reproducible, making it user friendly.

The present invention of a microfluidic device which generates an in vitro model of the human lymph node will largely improve the mechanistic studies of APC-lymphocyte interactions. In addition, it will provide an alternative to animal testing for examining the efficiency of newly synthesized drugs and a better prediction of a drug's ability to succeed in preclinical and clinical tests. Hence, it is both more time efficient and cost efficient. Furthermore, it will pave the way for countless immunology applications, leading to increased developments in biomedical research.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, and to thereby enable others skilled in the art to best utilize the present invention and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the present invention.

The invention claimed is:

1. A 3D microfluidic device mimicking lymph node anatomy and physiology comprising:
   a body defining a substantially circular central cavity, an inlet aperture and an outlet aperture, wherein the apertures are positioned at opposing ends of the central cavity on a central axis of the body, wherein the central cavity comprises:
      a top cavity configured to mimic a follicle of the lymph node;
      a bottom cavity configured to mimic a paracortex of the lymph node;
      a first plurality of micro-pillars in an arcuate arrangement around the top and bottom cavities;
      a second plurality of micro-pillars transversely positioned to the central axis between the top and bottom cavities and bounded by the first plurality of micro-pillars;
      a third plurality of micro-pillars in a concentric arrangement to the first plurality of micro-pillars;
      a first channel configured to mimic a subcapsular sinus of a lymph node, positioned between the third plurality of micro-pillars and an inner wall of the central cavity; and
      a second channel configured to mimic a reticular network of the lymph node positioned concentrically between the second and third pluralities of micro-pillars.

2. The microfluidic device of claim 1, wherein the distance between micropillars is about 0.2 mm.

3. The microfluidic device of claim 1, wherein the inlet aperture and the outlet aperture allow for injection of at least one of fluid, gas and solid material within and through the device.

4. The microfluidic device of claim 1, wherein the device is configured to be filled with cellular components in the first channel, second channel, top cavity and bottom cavity.

5. The microfluidic device of claim 1, further comprising an outer surface for sealing the device to a support base.

6. The microfluidic device of claim 1, further comprising a support base, optionally a glass support base.

7. The microfluidic device of claim 1, wherein the device comprises a material selected from a group consisting of glass, silicon, polysiloxane, and optically transparent polymers.

8. The microfluidic device of claim 7, wherein the body comprises polydimethylsiloxane (PDMS).

9. The microfluidic device of claim 1, wherein the width of the first channel is smaller than the width of the second channel.

10. The microfluidic device of claim 1, wherein the first channel, second channel, bottom cavity and top cavity of the device are adapted to support the adhesion of a hydrogel.

11. The microfluidic device of claim 1, wherein the top cavity is configured to accommodate viable B cells and the bottom cavity is configured to accommodate viable T cells.

12. A lab-on-a-chip comprising a 3D microfluidic device mimicking lymph node anatomy and physiology, wherein the microfluidic device comprises:
   a body defining a substantially circular central cavity, an inlet aperture and an outlet aperture, wherein the apertures are positioned at opposing ends of the central cavity on a central axis of the body, wherein the central cavity comprises:
      a top cavity configured to mimic a follicle of the lymph node;
      a bottom cavity configured to mimic a paracortex of the lymph node;
      a first plurality of micro-pillars in an arcuate arrangement around the top and bottom cavities;
      a second plurality of micro-pillars transversely positioned to the central axis between the top and bottom cavities and bounded by the first plurality of micro-pillars;
      a third plurality of micro-pillars in a concentric arrangement to the first plurality of micro-pillars;
      a first channel configured to mimic a subcapsular sinus of a lymph node, positioned between the third plurality of micro-pillars and an inner wall of the central cavity; and
      a second channel configured to mimic a reticular network of the lymph node positioned concentrically between the second and third pluralities of micro-pillars; and
      wherein the device is sealed to a glass support base.

13. The lab-on-a-chip of claim 12, wherein the inlet aperture and the outlet aperture allow for injection of at least one of fluid, gas and solid material within and through the device.

14. The lab-on-a-chip of claim 12, wherein the device comprises a material selected from a group consisting of glass, silicon, polysiloxane and optically transparent polymers, optionally wherein the polysiloxane is polydimethylsiloxane (PDMS).

15. The lab-on-a-chip of claim 12, wherein the width of the first channel is smaller than the width of the second channel.

16. The lab-on-a-chip of claim 12, further comprising hydrogels contained separately within the first channel, second channel, bottom cavity and top cavity of the device.

17. The lab-on-a-chip of claim 16, wherein the second channel comprises a porous hydrogel of Type I collagen.

18. The lab-on-a-chip of claim 16, wherein the hydrogel of the top cavity comprises viable B cells, and the hydrogel of the bottom cavity comprises viable T cells.

19. The lab-on-chip of claim 16, wherein the top cavity further comprises chemokine CXCL13.

20. The lab-on-chip of claim 16, wherein the bottom cavity further comprises a chemokine selected from the group consisting of CXCL12, CCL21, and CCL19, or a combination thereof.

* * * * *